United States Patent
Berting et al.

(10) Patent No.: US 7,135,874 B2
(45) Date of Patent: *Nov. 14, 2006

(54) SYSTEM AND METHOD FOR ENHANCED MEASUREMENT OF RHEOLOGICAL PROPERTIES

(75) Inventors: John Berting, Wilmington, DE (US); Ron Garritano, Monroe Township, NJ (US)

(73) Assignee: Waters Investments Limited, New Castle, DE (US)

(*) Notice: Subject to any disclaimer, the term of this patent is extended or adjusted under 35 U.S.C. 154(b) by 146 days.

This patent is subject to a terminal disclaimer.

(21) Appl. No.: 10/912,092

(22) Filed: Aug. 6, 2004

(65) Prior Publication Data
US 2006/0027738 A1    Feb. 9, 2006

(51) Int. Cl.
*G01R 27/26* (2006.01)
*G01B 7/30* (2006.01)
*G01D 5/24* (2006.01)
*G01D 5/241* (2006.01)

(52) U.S. Cl. ..................... 324/690; 324/662

(58) Field of Classification Search .............. 324/690, 324/660, 662, 683
See application file for complete search history.

(56) References Cited

U.S. PATENT DOCUMENTS

| | | | |
|---|---|---|---|
| 3,238,523 A | 3/1966 | Masel et al. | |
| 3,717,869 A | 2/1973 | Batz | |
| 3,766,544 A | 10/1973 | Batz | |
| 3,774,238 A | 11/1973 | Hardway, Jr. | |
| 4,238,781 A * | 12/1980 | Vercellotti et al. | 324/660 |
| 4,418,347 A | 11/1983 | Tanaka et al. | |
| 4,429,307 A | 1/1984 | Fortescue | |
| 4,477,810 A | 10/1984 | Tanaka et al. | |
| 4,563,683 A | 1/1986 | Tanaka et al. | |
| 4,631,524 A | 12/1986 | Brooke et al. | |
| 4,692,614 A * | 9/1987 | Wilson et al. | 250/231.1 |
| 4,694,275 A | 9/1987 | Cox | |
| 4,743,902 A | 5/1988 | Andermo | |
| 4,864,295 A | 9/1989 | Rohr | |
| 4,878,013 A * | 10/1989 | Andermo | 324/690 |
| 4,879,552 A * | 11/1989 | Arai et al. | 340/870.37 |
| 4,882,536 A | 11/1989 | Meyer | |
| 4,959,615 A | 9/1990 | Andermo | |
| 4,972,725 A | 11/1990 | Choisent | |
| 5,028,875 A * | 7/1991 | Peters | 324/660 |
| 5,315,865 A | 5/1994 | Hornfeck et al. | |

(Continued)

FOREIGN PATENT DOCUMENTS

EP    0 241 913    10/1987

(Continued)

*Primary Examiner*—Anjan Deb
(74) *Attorney, Agent, or Firm*—Pillsbury Winthrop Shaw Pittman LLP

(57) ABSTRACT

A sensor for measurement of small-angle or small-displacement position of a rotational rheometer incorporates multiple independent capacitors in a symmetric relationship. The device presents its output as a standard bridge configured differential signal, which can be interpreted and measured using conventional electronic demodulation means. The device includes an excitation array, a measurement array and an active rotor array. The active rotor array is coupled to a drive shaft of the rotational rheometer and measured relative to the measurement and excitation arrays. The active rotor array is driven by an electrical signal that is precisely matched to signals detected by the measurement array. By driving the active array with signals sensed by the measurement array, the sensor allows for reduced sensitivity to unwanted signals not in the measurement direction.

19 Claims, 5 Drawing Sheets

U.S. PATENT DOCUMENTS

| | | | |
|---|---|---|---|
| RE34,741 E | | 9/1994 | Andermo |
| 5,610,325 A | | 3/1997 | Rajagopal et al. |
| 5,631,409 A | * | 5/1997 | Rajagopal et al. ......... 73/54.35 |
| 5,657,006 A | | 8/1997 | Kinoshita et al. |
| 5,691,646 A | | 11/1997 | Sasaki |
| 5,731,707 A | * | 3/1998 | Andermo .................... 324/660 |
| 5,964,526 A | * | 10/1999 | Schramm ..................... 366/96 |
| 6,118,283 A | * | 9/2000 | Cripe ........................ 324/660 |
| 6,218,803 B1 | | 4/2001 | Montagu et al. |
| 6,492,911 B1 | | 12/2002 | Netzer |
| 2002/0014891 A1 | * | 2/2002 | Brasseur ..................... 324/660 |
| 2006/0028215 A1 | * | 2/2006 | Berting et al. .............. 324/662 |

FOREIGN PATENT DOCUMENTS

| | | |
|---|---|---|
| JP | 60088314 | 5/1985 |
| JP | 03061816 | 3/1991 |
| JP | 05264291 | 10/1993 |

* cited by examiner

SYSTEM AND METHOD FOR ENHANCED MEASUREMENT OF RHEOLOGICAL PROPERTIES

BACKGROUND

1. Field of the Invention

Embodiments of the present invention relate to systems and methods for capacitive measurement using a rheometer. More particularly, embodiments of the present invention relate to systems and methods for measuring the rheological properties of a sample on a rotational rheometer, while exhibiting a reduced sensitivity to motions that are not in the direction or axis of the desired measurement.

2. Background of the Invention

Rotary rheometers, viscometers or viscosimeters are typically used to measure rheological properties of materials, such as their viscosity, compliance, and modulus, by rotating, deflecting or oscillating a measuring geometry in a material, either by applying a torque and measuring the resultant velocity or displacement, or by applying a velocity or displacement and measuring the resultant torque. The torque and velocity/displacement are used in conjunction with measuring geometry factors to determine the properties of the material.

As used herein, the term "rheometer" includes rheometers, viscometers, viscosimeters and similar instruments that are used to measure the properties of fluid or similar materials (see list below). Viscosity is an internal property of a fluid that offers resistance to flow (i.e., it concerns the thickness of a liquid).

The term "material," as used herein, includes liquids, oils, dispersions, suspensions, emulsions, adhesives, biological fluids, polymers, gels, pastes, slurries, melts, resins, powders or mixtures thereof. Such materials are also referred to herein as "fluids." More specific examples of materials include asphalt, chocolate, blood, drilling mud, lubricants, oils, greases, photoresists, liquid cements, elastomers, thermoplastics, thermosets and coatings.

A common use for a rheometer is to determine fluid properties of a material. One technique is to apply a torque developed by a motor in the presence of the material, and measure the resultant velocity or displacement. The torque and velocity/displacement are used in conjunction with measuring geometry factors to determine the properties of the material. Thus, the rheometer requires a position sensor that is extremely accurate, linear, stable and consistent. The position sensor must operate over a very small range of motion with a high resolution of position.

Unfortunately, current rotary rheometers use sensors that suffer from gain error. Specifically, mechanical motions that are not in the axis of the primary measurement cause parasitic capacitance that can be reported erroneously as a change of the primary measurement axis. Thus, it is desirable to create small-angle or small-displacement capacitive sensors that have greatly reduced sensitivity to typical sources of mechanical positioning error.

BRIEF SUMMARY OF THE INVENTION

A device for measuring movement of a rheometer according to the present invention includes three components: an excitation array, an active rotor array, and a measurement array. The active rotor array is positioned between the measurement and excitation arrays and mechanically coupled to a drive shaft of the rheometer. The position of the active rotor array element is measured relative to the measurement and excitation arrays. Particularly, the measurement array senses a signal from the excitation array, which is affected as the active rotor array moves with the drive shaft.

In a preferred embodiment of the invention, sensitivity may be increased by using a plurality of elements in each array of the device. For example, the excitation array may have a plurality of first emitters and a plurality of second emitters. Each first emitter emits a first sinusoidal signal, and each second emitter emits a second sinusoidal signal, with the second sinusoidal signal out of phase with the first sinusoidal signal.

Similarly, the measurement array has a plurality of first detectors and a plurality of second detectors. Each first detector senses a first voltage of the first sinusoidal signal and the second sinusoidal signal, and each second detector senses a second voltage of the first sinusoidal signal and the second sinusoidal signal. Likewise, the active rotor array has a plurality of movable electrodes, wherein movement of the plurality of movable electrodes varies the first voltage and the second voltage sensed by the measurement array.

In a preferred embodiment of the present invention, each array (e.g., the excitation array, measurement array, and active rotor/linear array) uses fifty blades, increasing the resulting sensitivity by a factor of twenty-five.

In a preferred embodiment of the invention, the active rotor array is driven by the voltages sensed by the measurement array. Driving the active array with the voltages of the measurement array causes rejection of unwanted signals that are not in the measurement direction. Thus, for angular measurement of the movement of the drive shaft, axial motion of an active rotor does not result in an amplitude change in the differential output signal. Lateral translation of an active rotor does not simulate an angle change due to the plurality of capacitive elements and the resultant cancellation of capacitance changes due to averaging effects.

Multiple capacitive elements of the sensor that combine into a single composite measurement provide increased sensitivity. Similarly, driving the active array with voltages from the measurement array results in reduced sensitivity to other mechanical motions that are not in the direction of measurement. Although the invention is described in a rheology application, the invention may be used in any application in which small angles or small distances are measured.

DETAILED DESCRIPTION OF THE INVENTION

A rheometer according to the present invention includes a measurement device having an excitation array, an active rotor array, and a measurement array. The active rotor array is positioned between the measurement and excitation arrays and mechanically coupled to a rotating shaft of the rheometer so that it rotates with the shaft. The position of the active rotor array is measured relative to the measurement and excitation arrays. Particularly, the measurement array senses a signal from the excitation array, which is affected as the active rotor/linear array moves from side to side.

When the active rotor is turned relative to the excitation and measurement arrays, a signal is produced on the measurement array that is proportional to the change in angular position. Changes to the position of the active rotor that are not angular in nature produce greatly reduced output signal changes. For example, axial motion of the active rotor does not result in an amplitude change in the differential output signal. Similarly, lateral translation of the active rotor does not simulate an angle change. The measurement device also has increased sensitivity by a factor of 20 or more.

Figure 1:
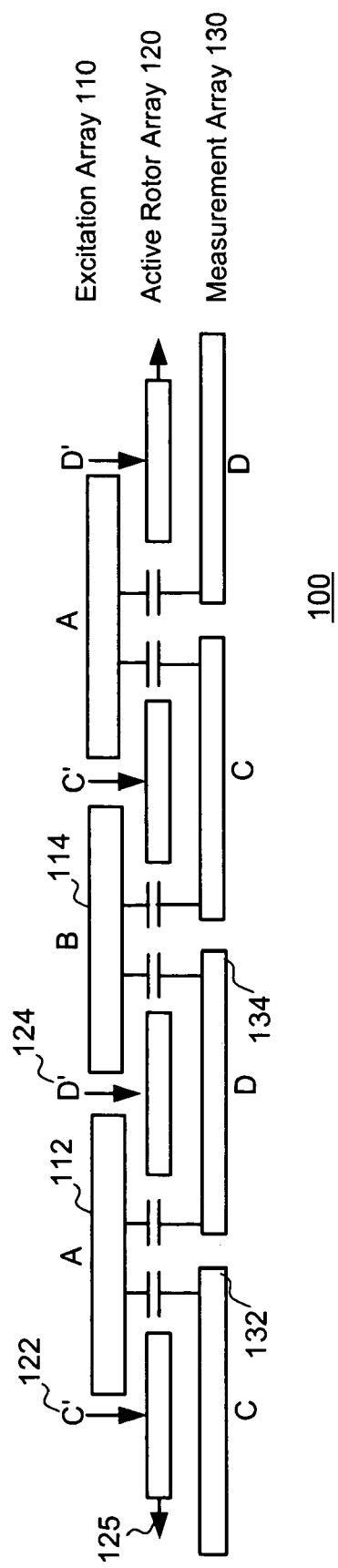
FIG. 1 is a cutaway view of a small portion of a measurement device according to a preferred embodiment of the present invention.

FIG. 1 is a cutaway view of a small portion of a small angle measurement device used in a rotational rheometer according to a preferred embodiment of the present invention. Measurement device 100 comprises an excitation array 110, an active rotor array 120 and a measurement array 130. Active rotor array 120 is positioned between excitation array 110 and measurement array 130. Although not shown in FIG. 1, active rotor array 120 mechanically couples, for example, to a drive shaft of a motor in a rotational rheometer. Thus, active rotor array 120 moves with the drive shaft of the rheometer.

Each array of the measurement device 100 (i.e., excitation array 110, active rotor array 120 and measurement array 130) has a plurality of elements or conductive areas, shown in more detail in FIGS. 2A–2C described below.

In a preferred embodiment of the invention, measurement device 100 operates with a maximum linear range of plus or minus 20 milliradians (mRad), which is used for a 3.5 to 5.0 mRad transducer. Measurement device 100 has an outer diameter of three inches for the assembly using PC board technology. More particularly, each array has a clear hole with a minimum diameter of 1.0 inches for a hub and wiring. In a preferred embodiment, the clear hole is 1.5 inches. Additionally, each array has an outer diameter of 2.5 inches.

Excitation array 110 is the electrically driven element of the measurement device 100. Particularly, excitation array 110 provides a sinusoidal signal to measurement array 130. Emitter A 112 and emitter B 114, elements of excitation array 110, emit sine signals that are 180 degrees out-of-phase.

Active rotor array 120 is a conductive element of the measurement device 100 used as a shadowing element to block the electrostatic field generated by excitation array 110. Arrows 125 indicate the side-to-side motion of active rotor array 120 in the desired axis of measurement. For position determination, active rotor array 120 is mechanically coupled to the moving shaft of the rheometer, whose motion is being measured. Unlike conventional capacitive measurement devices, active rotor array 120 is driven by electric signals C' 122 and D' 124 to reduce the parasitic capacitance that causes gain error.

Measurement array 130 senses a signal from excitation array 110, which is transferred by a capacitive coupling across the gap between the two arrays. The elements of measurement array 130 include detector C 132 and detector D 134. Buffer amplifiers (not shown) are connected to nodes C 132 and D 134 to drive the C' 122 and D' 124 signals, respectively. Accordingly, nodes C' 122 and D' 124 are low impedance sources precisely matched to the signals appearing on nodes C and D.

Figure 2A:
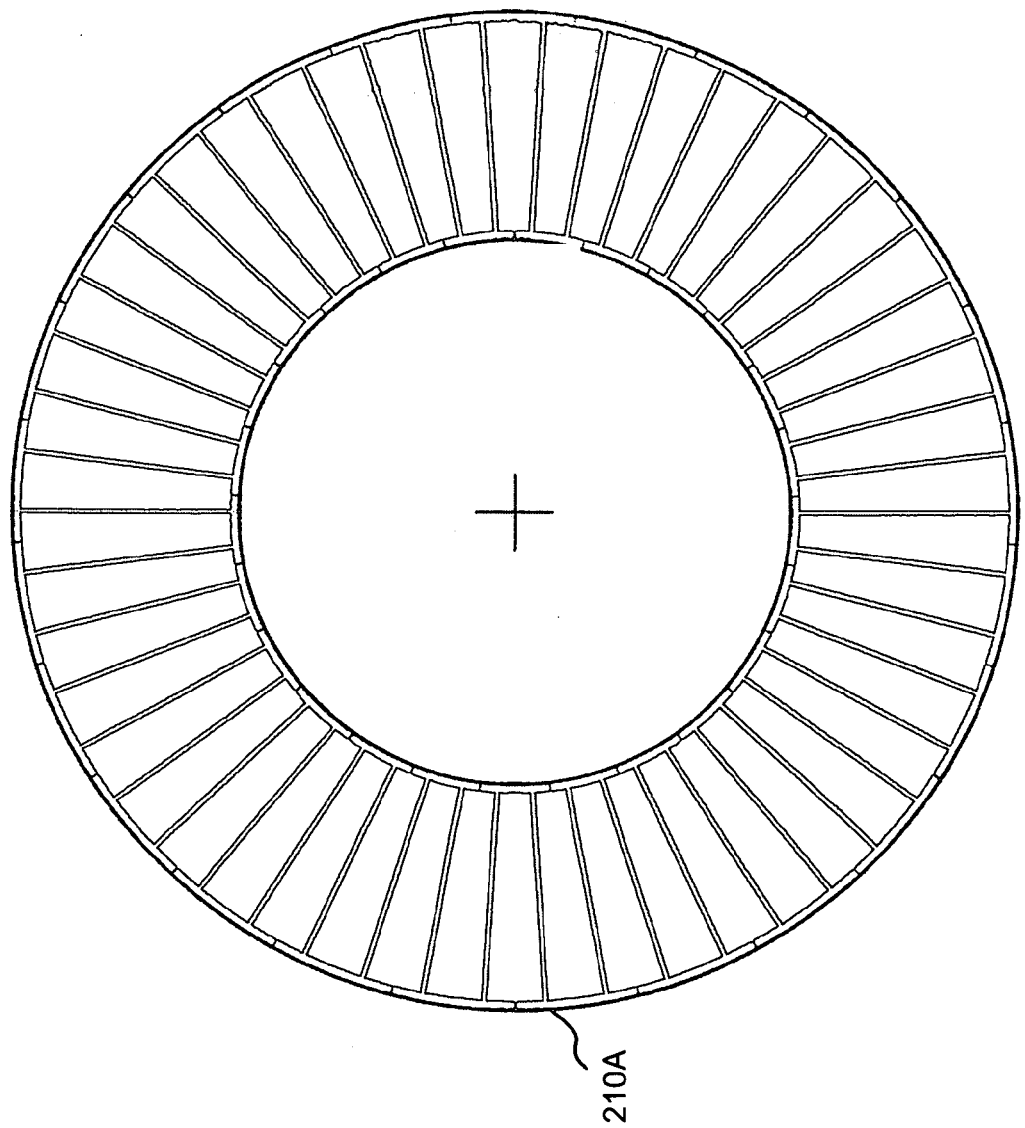
FIGS. 2A, 2B and 2C are schematic diagrams of an exemplary excitation array, an exemplary active rotor array and an exemplary measurement array, respectively according to a preferred embodiment of the present invention.
Figure 2B:
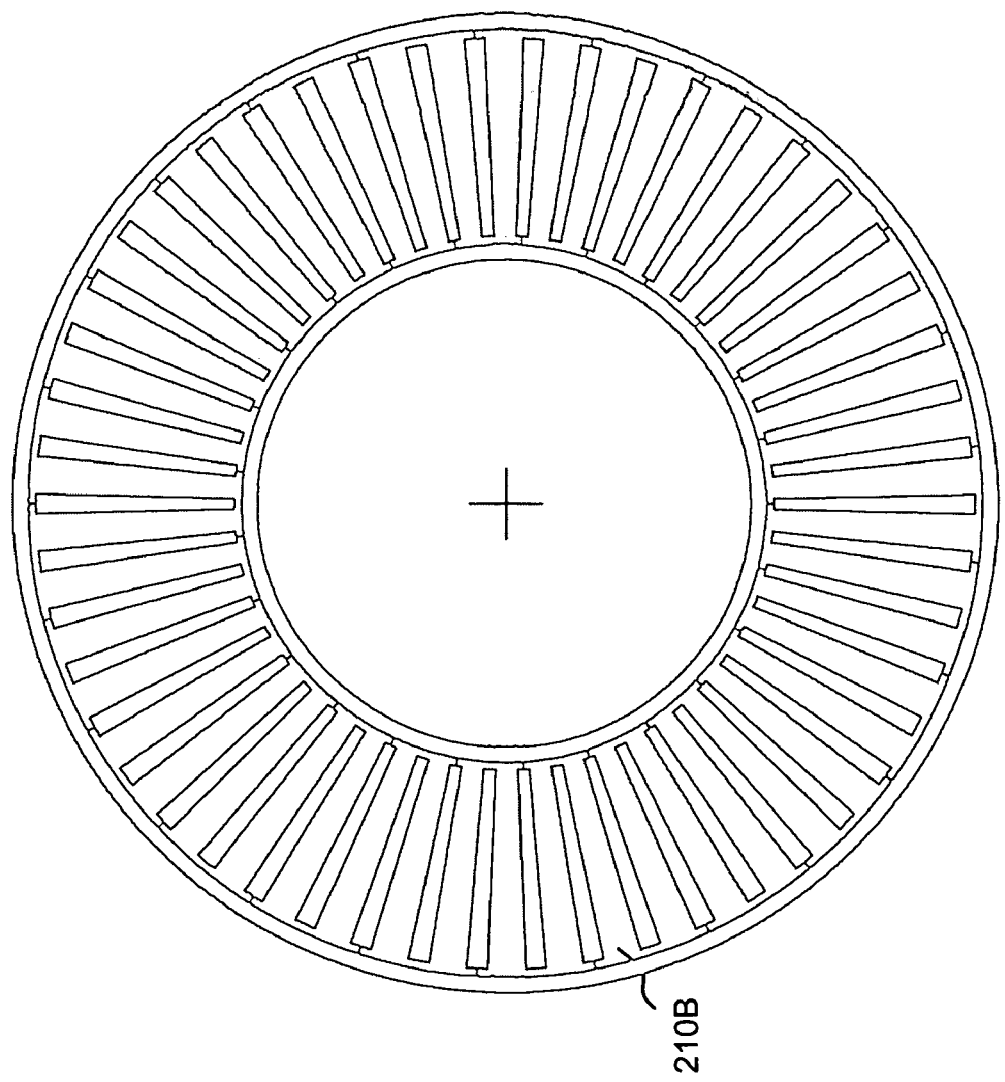
Figure 2C:
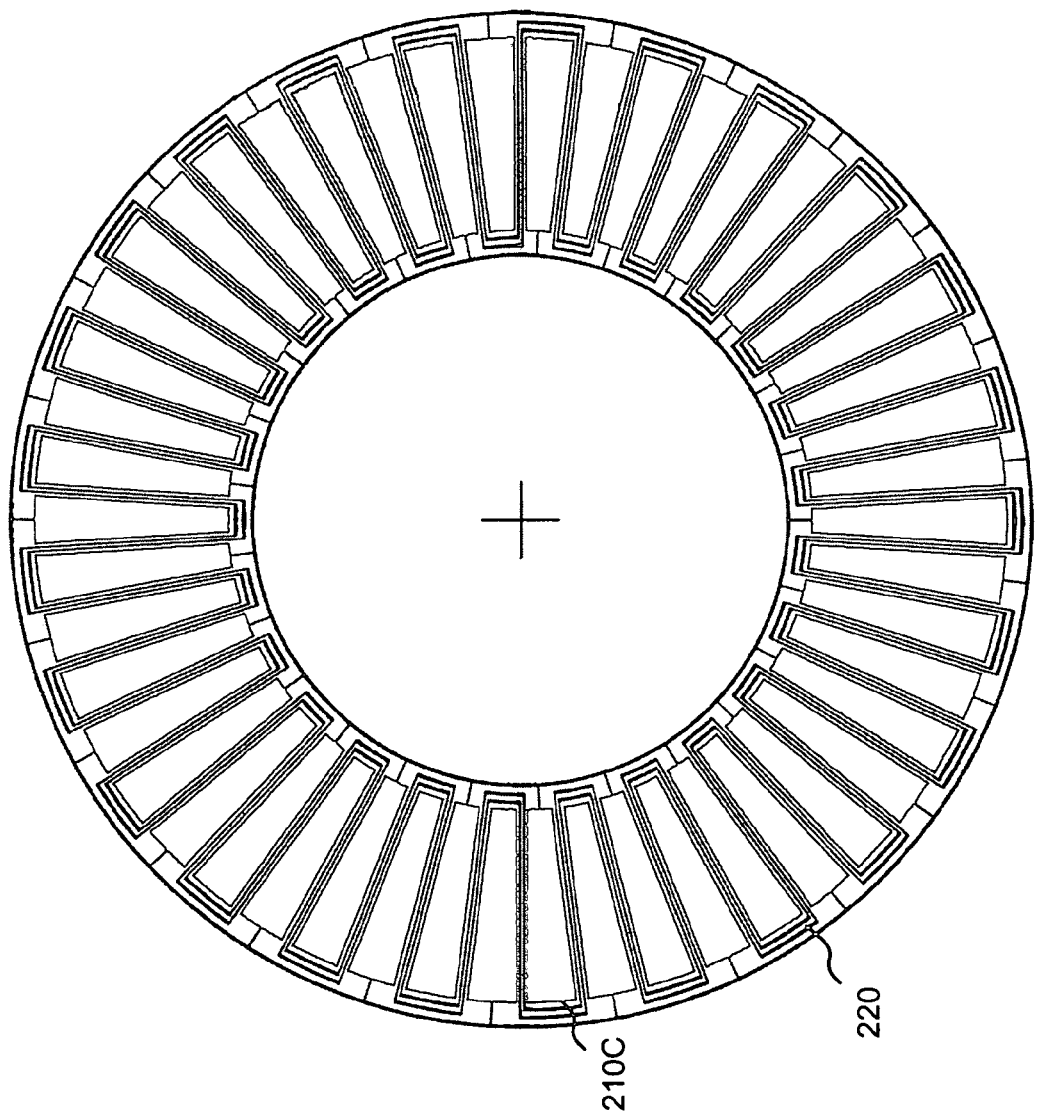

FIGS. 2A, 2B and 2C are schematic diagrams of excitation array 110, active rotor array 120 and measurement array 130, respectively, according to a preferred embodiment of the present invention. In the example illustrated in these figures, excitation array 110, active rotor array 120 and measurement array 130 each have 50 elements or conductive areas called blade 210A, 210B and 210C. Each blade measures 0.1256637 radians. In addition, each blades 210C of measurement array 130 has two traces or double guards 220 that supply drive signal C' 122 and D' 124 to the active rotor array 120. The trace width and spacing between the blades is 0.005 inches.

Although the illustrative example discloses the use of 50 blades, one skilled in the art will recognize that the present invention is not limited as such. For example, in another embodiment, only 20 blades per array may be used. Alternatively, using thin-film and other small geometry fabrication methods, arrays with a greater density than 25 bridge elements (50 blades) can be achieved.

In the embodiment described herein, the use of 50 blades increases the resulting sensitivity by a factor of 25. Particularly, the capacitive elements of excitation array 110 and measurement array 130 form multiple capacitive bridges, described below in reference to FIG. 3. Each bridge includes the following nodes: emitter A, emitter B, detector C, detector D, displacement element C' and displacement element D'. The use of 50 excitation and measurement blades results in 25 such bridges composed of 100 capacitors, each bridge increasing the sensitivity of the measurement device.

Figure 3:
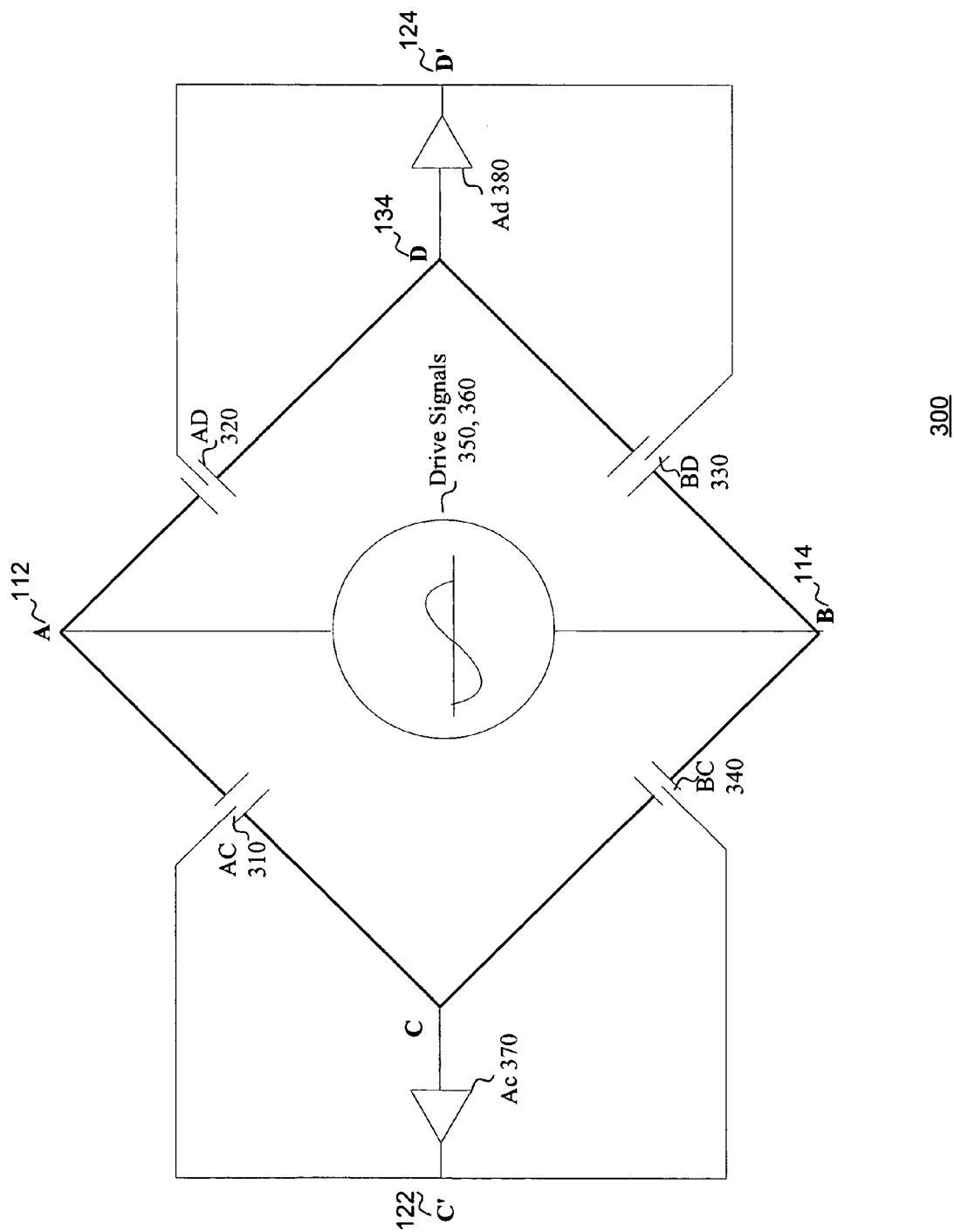
FIG. 3 is a schematic diagram of a capacitive bridge formed by the elements of the measurement device according to the preferred embodiment of the present invention.

FIG. 3 is a schematic diagram of a capacitive bridge formed by the elements of the measurement device according a preferred embodiment of the present invention. Capacitive bridge 300 includes nodes A, B, C and D, as well as displacement elements C' and D', variable capacitors AC 310, AD 320, BD 330 and BC 340, drive signals 350 and 360, and buffer amplifiers Ac 370 and Ad 380.

Drive signals 350 and 360 represent the sinusoidal signals emitted from emitter A 112 and emitter B 114 that are 180 degrees out-of-phase. Nodes C 132 and D 134 each detect the two signals 350 and 360 that are emitted from emitters A and B. The detected signals vary in strength and phase as the position of active rotor array 120 changes, and can be described as variable capacitors AC 310, AD 320, BD 330 and BC 340.

Variable capacitor AC 310 represents the capacitance between emitter A 112 and detector C 132 of FIG. 1. Similarly, variable capacitor AD 320 represents the capacitance between emitter A 112 and detector D 134. Variable capacitor BD 330 represents the capacitance between emitter B 114 and detector D 134, and variable capacitor BC 340 represents the capacitance between emitter B 114 and detector C 132. Each of the capacitors AC 310, AD 320, BD 330 and BC 340 are described as variable because their capacitance values vary with the movement of active rotor array 120.

For example, if active rotor array 120 of FIG. 1 moves to the left, then the elements of rotor array provide less shadowing between detector C 132 and emitter A 112 and less shadowing between detector D 134 and emitter B 114. Because shadowing is reduced by movement of active rotor array 120 to the left, detector C 132 receives greater exposure to emitter A 112 and detector D 134 receives greater exposure to emitter B 114. Accordingly, moving active rotor array 120 of FIG. 1 to the left increases the capacitance of capacitor AC 310 and BD 330, by increasing the effective surface area of the capacitive elements (i.e., the portion of the emitter and detector elements that are not shaded by the conductive rotor elements).

Similarly, moving active rotor array 120 of FIG. 1 to the left increases the shadowing provided by active rotor array 120 between emitter A 112 and detector D 134 as well as between emitter B 114 and element C 132. Accordingly, moving active rotor array 120 of FIG. 1 to the left decreases the capacitance of capacitor AD 320 and BC 340.

Returning to FIG. 3, as active rotor 120 moves to the left, bridge capacitors AC 310 and BD 330 increase in capacitance while bridge capacitors AD 320 and BD 340 decrease a proportional value in capacitance. The change in capacitance values of the bridge capacitors 310, 320, 330 and 340 causes bridge 300 to become unbalanced. Sense points or detectors C 132 and D 134 detect the differential signal of the unbalanced bridge 300. Further, the variation of capacitance is linear with respect to the horizontal displacement of the effective surface area of the various capacitive elements changes linearly.

Each capacitive bridge configuration formed by the various physical elements of FIG. 1 increases the sensitivity of the system to capacitance changes. Particularly, the use of multiple bridges multiplies the sensitivity of measurement device 100 by the number of array elements used. Particularly, as described above in reference to FIGS. 2A, 2B and 2C, a preferred embodiment of the present invention includes 50 blades for each array in the measurement device (i.e., excitation, active rotor and measurement arrays), resulting in 25 bridge elements composed of 100 capacitors connected in an array. Thus, the resulting sensitivity of the measurement device is multiplied by a factor of 25.

Although using more array elements increases sensitivity of the measuring device, it also decreases its full-scale angular or linear range. For example, if a single-capacitor rotary position sensor has a maximum full-scale range of 180 degrees, then an array of 25 bridge elements is reduced to a maximum full-scale range of 7.2 degrees (e.g., 180/25=7.2). However, physical limitations of fabrication size, alignment, the gap between plates, edge effects and other necessary design compromises limit the range of the sensor even further than the theoretical 7.2 degrees maximum full-scale range. The embodiment depicted in FIGS. 2A, 2B and 2C, comprising 50 blades per array achieves small angle measurement of plus or minus 20 mRad in limited range applications of 5 mRad or less.

Parasitic capacitances (e.g., introduced by movement in the non-measurement direction) could skew the signals detected at nodes C and D in the absence of corrective measures. For example, motion of the rotary electrode that is not along the primary measurement path can introduce additional capacitances that are parasitic to the function of the sensor, causing an error in gain and a reduced sensitivity. Particularly, low impedance nodes A and B would remain relatively unaffected by any changes in capacitance due to parasitic capacitance. However, high impedance nodes C and D that are extremely sensitive to capacitive loading would change their values if a parasitic capacitance were introduced, thereby resulting in a gain error in the bridge.

To reduce or eliminate any skewing, active rotor array 120 is electrically driven by elements C' 122 and D' 124. Elements C' 122 and D' 124 are low impedance elements that are relatively insensitive or immune to changes in capacitance due to capacitance loading. Buffer amplifiers 370 and 380 supply the detected signals from measurement array 130 to active rotor array 120. In this way, drive signals C' 122 and D' 124 are precisely matched to the signals appearing on nodes C 132 and D 134, respectively, of stationary measurement array 130.

Thus, parasitic capacitances formed by the arrangement of FIG. 1 include AC', AD', BC', BD', CC', CD', DC' and DD'. However, A, B, C' and D' nodes are emitter elements, which are low-impedance sources that remain relatively unaffected by any change of capacitance. Thus, although parasitic capacitances AC', AD', BC' and BD' are real capacitances that are affected by gap distance, any change in these capacitances will leave nodes A, B, C' and D' relatively unaffected.

Similarly, parasitic capacitances CD' and DC' are also minimized by their placement in the system. Particularly, the CD' and DC' capacitance is minimized by placing nodes C' 122 and D' 124 above the center of nodes C and D, respectively. Thus, even when active rotor array moves to the left or right the amount of any overlap between nodes C and D' or between nodes C' and D are minimized.

Most importantly, parasitic capacitances CC' and DD' are effectively zero. Notably, because node D' is driven from node D, the two sources have the same potential voltage at all times. Thus, the capacitance DD' between node D and D' is effectively zero. The same protection ("electrostatic guarding") exists between nodes C and C', resulting in a zero capacitance. The effective zero value for these two capacitors is not changed in any way by the gap between the two electrodes, which may change due to movement in a direction other than the measurement direction. Because these capacitances are normally the source of gain errors in a measurement device, this source of error is effectively eliminated from the measurement by the present invention.

In summary, the present invention increases sensitivity in the measurement direction and reduces error due to motion in the non-measurement direction. As described, the various physical elements of FIG. 1 form multiple capacitive bridges, each bridge increasing the sensitivity of the measurement device. When 50 blades are used, the resulting sensitivity of the measurement device is increased by a factor of 25.

In addition, the measurement device is improved to reduce the parasitic capacitance introduced by movement in the non-measuring direction by driving the active rotor array with an electric signal.

Accordingly, using the described multiple bridge technique and capacitive guarding of rotor elements, it is possible to fabricate a highly precise small-angle capacitive position sensor for use in a rheometer that is relatively insensitive to non-measurement-axis motions. Using traditional printed circuit board techniques it is possible to achieve an array of 25 elements in a reasonable operating diameter. As described above, higher density arrays can be achieved using thin-film and other small geometry fabrication methods.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A capacitive rotation angle sensor for measuring a movement in a rotational rheometer, comprising:
   an excitation array having a plurality of first emitters and a plurality of second emitters, the plurality of first emitters emitting a first sinusoidal signal, and the plurality of second emitters emitting a second sinusoidal signal, the second sinusoidal signal being out of phase with the first sinusoidal signal;
   a measurement array arranged opposite to the excitation array and having a plurality of first detectors and a plurality of second detectors, the plurality of first detectors sensing a first voltage of the first and second sinusoidal signals and the plurality of second detectors sensing a second voltage of the first and second sinusoidal signals; and
   an active rotor array that is adapted to be mechanically coupled to a drive shaft of the rotational rheometer and rotationally moved between the excitation array and the measurement array, the active rotor array having a plurality of first movable elements and a plurality of second movable elements, the plurality of first movable elements being driven by the first voltage and the plurality of second movable elements being driven by the second voltage,
   wherein movement of the active rotor array varies the first and second voltages and the active rotor array determines the movement of the drive shaft of the rotational rheometer from the first and second voltages.

2. The capacitive rotation angle sensor of claim 1, wherein the excitation array, the active rotor array, and the measurement array are formed using printed circuit board techniques.

3. The capacitive rotation angle sensor of claim 1, wherein the excitation array, the active rotor array, and the measurement array are formed using a thin-film fabrication method.

4. The capacitive rotation angle sensor of claim 1, wherein the excitation array, the measurement array and the active rotor array are in the form of plates.

5. The capacitive rotation angle sensor of claim 1, wherein the excitation array comprises 20 or more emitters, the active rotor array comprises 20 or more movable electrodes, and the measurement array comprises 20 or more detectors, thereby forming 10 or more capacitive bridges.

6. The capacitive rotation angle sensor of claim 1, wherein the sensor has a maximum range of plus or minus 20 milliradians.

7. A method for measuring a small angle movement of a rotational rheometer, comprising:
   emitting a first sinusoidal signal from a first emitter of an excitation array;
   emitting a second sinusoidal signal from a second emitter of the excitation array, the second sinusoidal signal being out of phase with the first sinusoidal signal;
   sensing a first voltage of the first and second sinusoidal signals at a first detector in a measurement array, the measurement array being arranged opposite to the excitation array
   sensing a second voltage of the first and second sinusoidal signals at a second detector in the measurement array;
   rotationally moving an active rotor array, which is adapted to be mechanically coupled to a drive shaft of the rotational rheometer, between the excitation array and the measurement array, the active rotor array having a first movable electrode and a second movable electrode, wherein movement of the first and second movable electrodes varies the first voltage and the second voltage sensed by the measurement array and the measurement array determines the small angle movement of the drive shaft of the rotational rheometer from the first and second voltages;
   driving the first movable electrode with the first voltage; and
   driving the second movable electrode with the second voltage.

8. The method of claim 7, wherein the excitation array further comprises a plurality of first emitters and a plurality of second emitters,
   wherein the active rotor array comprises a plurality of first movable electrodes and a plurality of second movable electrodes, and
   the measurement array comprises a plurality of first detector elements and a plurality of second detector elements.

9. The method of claim 7, wherein the excitation array comprises 20 or more emitters, the active rotor array comprises 20 or more movable electrodes, and the measurement array comprises 20 or more detectors.

10. The method of claim 7, wherein the excitation array, the active rotor array, and the measurement array are formed using printed circuit board techniques.

11. The method of claim 7, wherein the excitation array, the active rotor array, and the measurement array are formed using a thin-film fabrication method.

12. The method of claim 7, wherein the excitation array, the measurement array and the active rotor array are in the form of plates, each plate comprising a plurality of blades.

13. A capacitive rotation angle sensor for measuring a small angle movement of a rotational rheometer, comprising:
   means for emitting a first sinusoidal signal from a first emitter of an excitation array;
   means for emitting a second sinusoidal signal from a second emitter of the excitation array, the second sinusoidal signal being out of phase with the first sinusoidal signal;
   means for sensing a first voltage of the first and second sinusoidal signals at a first detector in a measurement array, the measurement array being arranged opposite to the excitation array;
   means for sensing a second voltage of the first and second sinusoidal signals at a second detector in the measurement array;
   means for rotationally moving an active rotor array, which is adapted to be mechanically coupled to a drive shaft of the rotational rheometer, between the excitation array and the measurement array, the active rotor array having a first movable electrode and a second movable electrode, wherein movement of the first and second movable electrodes varies the first voltage and the second voltage sensed by the measurement array;
   means for determining the small angle movement of the drive shaft of the rotational rheometer from the first and second voltages;

means for driving the first movable electrode with the first voltage; and means for driving the second movable electrode with the second voltage.

14. The capacitive rotor angle sensor of 13, wherein the excitation array further comprises a plurality of first emitters and a plurality of second emitters, wherein the active rotor array comprises a plurality of first movable elements and a plurality of second movable elements, and wherein the measurement array comprises a plurality of first detector elements and a plurality of second detector elements.

15. The capacitive rotation angle sensor of claim 14, wherein the excitation array comprises 20 or more emitters, the active rotor array comprises 20 or more movable electrodes, and the measurement array comprises 20 or more detectors.

16. The capacitive rotation angle sensor of claim 13, wherein the excitation array, the active rotor array, and the measurement array are formed using printed circuit board techniques.

17. The capacitive rotation angle sensor of claim 13, wherein the excitation array, the active rotor array, and the measurement array are formed using a thin-film fabrication method to achieve high density.

18. The capacitive rotation angle sensor of claim 13, wherein the excitation array, the measurement array and the active rotor array are in the form of plates, each plate comprising a plurality of blades.

19. The capacitive rotation angle sensor of claim 13, wherein the sensor has a maximum range of plus or minus 20 milliradians.

* * * * *